United States Patent
Maron et al.

(10) Patent No.: US 11,278,479 B2
(45) Date of Patent: Mar. 22, 2022

(54) MOISTURIZING ANHYDROUS BUTTER BALM COMPOSITION AND METHOD

(71) Applicant: L'OREAL, Paris (FR)

(72) Inventors: Zachary Maron, Jersey City, NJ (US); Allison Nicole Elder, North Plainfield, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/895,968

(22) Filed: Jun. 8, 2020

(65) Prior Publication Data

US 2020/0297599 A1 Sep. 24, 2020

Related U.S. Application Data

(63) Continuation-in-part of application No. 16/141,599, filed on Sep. 25, 2018, now Pat. No. 11,039,993.

(60) Provisional application No. 62/983,483, filed on Feb. 28, 2020.

(51) Int. Cl.

| | | |
|---|---|---|
| *A61K 8/34* | (2006.01) | |
| *A61Q 5/00* | (2006.01) | |
| *A61K 8/37* | (2006.01) | |
| *A61K 8/92* | (2006.01) | |
| *A61K 8/97* | (2017.01) | |
| *A61K 8/04* | (2006.01) | |
| *A61K 8/86* | (2006.01) | |

(52) U.S. Cl.
CPC .............. *A61K 8/345* (2013.01); *A61K 8/04* (2013.01); *A61K 8/375* (2013.01); *A61K 8/86* (2013.01); *A61K 8/922* (2013.01); *A61K 8/97* (2013.01); *A61Q 5/00* (2013.01); *A61K 2800/31* (2013.01); *A61K 2800/59* (2013.01)

(58) Field of Classification Search
None
See application file for complete search history.

(56) References Cited

U.S. PATENT DOCUMENTS

| | | |
|---|---|---|
| 5,160,738 A | 11/1992 | Macaulay et al. |
| 6,503,944 B1 | 1/2003 | Chanchani |
| 7,195,787 B1 | 3/2007 | Pykett et al. |
| 8,512,683 B2 | 8/2013 | SaNogueira et al. |
| 8,524,211 B1 | 9/2013 | Rafiee et al. |
| 2007/0286908 A1* | 12/2007 | Clampitt ............... A61K 36/00 424/680 |
| 2010/0074965 A1 | 3/2010 | Erisson nee Conry et al. |
| 2011/0152372 A1 | 6/2011 | Mallard et al. |
| 2017/0143616 A1* | 5/2017 | Page ....................... A61Q 1/00 |
| 2017/0172904 A1 | 6/2017 | Page et al. |
| 2017/0252288 A1* | 9/2017 | Lesniak ................. A61K 8/927 |

FOREIGN PATENT DOCUMENTS

| | | | |
|---|---|---|---|
| FR | 2966360 A1 | 4/2012 | |
| FR | 2968980 A1 * | 6/2012 | ........... A61K 8/0229 |

OTHER PUBLICATIONS

Edinson Yara-Varon et al. "Vegetable Oils as Alternative Solvents for Green Oleo-Extraction, Purification and Formulation of Food and Natural Products", Molecules, vol. 22, No. 9, Sep. 5, 2017, p. 1474.
Mintel; Feb. 20, 2018, anonymous: "Macadamia Nut Pomegranate Lip Balm", retrieved from www.gnpd.com.
International Search Report issued for PCT/US2019/052606 dated Jan. 2, 2020.
Dans Mintel, Hydrogenated Vegetable Oil et Tribehenin et Glyceryl Stearate et Glyceryl Behenate NOT Aqua et soins de la peau = 1 produit (Exozen-Hydrating Face Mask), Jul. 2012.

* cited by examiner

*Primary Examiner* — Celeste A Roney
(74) *Attorney, Agent, or Firm* — McNees Wallace & Nurick LLC

(57) ABSTRACT

A hydrating cosmetic composition for keratinous substrates that includes a stabilized anhydrous balm that includes at least one glycol humectant dispersed in a stabilized anhydrous fatty phase that includes at least one plant derived butter, a blend of structuring waxes, and a blend of fatty compounds and a surfactant.

20 Claims, No Drawings

MOISTURIZING ANHYDROUS BUTTER BALM COMPOSITION AND METHOD

PRIORITY CLAIM AND RELATED APPLICATIONS

This application claims the benefit under 35 U.S.C. § 119(e) and priority to U.S. Provisional Patent Application Ser. No. 62/983,483, filed on Feb. 28, 2020, entitled MOISTURIZING ANHYDROUS BUTTER BALM COMPOSITION AND METHOD, the entirety of which is incorporated by reference herein. This application is a continuation in part of and claims priority to U.S. patent application Ser. No. 16/141,599 entitled COMPOSITIONS WITH NATURAL OILS FOR PROVIDING A PROTECTIVE BARRIER filed on Sep. 25, 2018, the entirety of which is incorporated by reference herein.

FIELD OF THE INVENTION

The invention relates to an anhydrous balm composition containing high levels of moisturizing humectant dispersed and suspended in a stable formulation that provides moisture and protection when applied to keratinous substrates, for example, human skin and human hair.

BACKGROUND OF THE INVENTION

Topical formulations for keratinous substrates, for example skin, can include high amounts of fatty emollients that provide a protective occlusive effect as a barrier that prevents water loss and incursion of irritants and contaminants. Such formulations can have aesthetic and tactile drawbacks of being too soft and loose on pickup, and melting too readily upon application, such as, to the skin, resulting in a thin and oily feeling. In addition, because of the high amount of oils, dispersion of humectants such as glycols can be difficult, which limits the ability to provide moisturizing benefits.

There is a need for a composition that overcomes one or more of the aforementioned drawbacks. Such a composition would provide one or more of good spreadability, and tactile and aesthetic properties that include a rich, buttery texture on pickup and pleasant feel on skin, and deliver the moisturizing benefits of included humectants.

BRIEF SUMMARY OF THE INVENTION

The summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

The hydrating cosmetic composition and methods of making them are characterized, in various embodiments.

In accordance with a first embodiment, a hydrating cosmetic composition for keratinous substrates is provided, which includes a stabilized anhydrous balm that includes:
  a) at least one glycol humectant present in an amount from at least about 10%, by weight, based on the total weight of the composition, the glycol humectant dispersed in a stabilized anhydrous fatty phase; and
  b) a stabilized anhydrous fatty phase comprising:
    i) at least one plant derived butter present in an amount from at least about 20%, by weight, based on the total weight of the composition;
    ii) a blend of structuring waxes comprising at least one nature derived wax and hydrogenated vegetable oil, the structuring waxes present in a ratio of nature derived wax to hydrogenated vegetable oil in a range from about 3:1 to about 1:3;
    iii) a blend of fatty compounds comprising glyceryl dibehenate, tribehenin and glyceryl behenate, and two or more fatty compounds selected from triglycerides and plant derived oils having a chain length from and including C8 to C24, the blend of fatty compounds, in combination, present in the composition in an amount from about 10% to about 50%, by weight, based on the total weight of the composition; and
    iv) a surfactant comprising glyceryl stearate.

In some embodiments, the stabilized anhydrous balm is characterized as being stabilized as demonstrated by an absence of visible droplets and crystals after about eight weeks at 45° C.

In some embodiments, the at least one glycol humectant comprises glycerin and is present in the composition in an amount from at least about 10% and to about 25%, by weight, based on the total weight of the composition.

In some embodiments, the at least one glycol humectant further comprises a glycol solvent selected from the group consisting of propanediol, caprylyl glycol, polypropylene glycol, and combinations thereof.

In some embodiments, the glycol solvent comprises propanediol and is present in the composition in an amount from about 1% to about 10%, by weight, based on the total weight of the composition.

In some embodiments, the at least one plant derived butter comprises a blend of two or more plant derived butters, each plant derived butter present in an amount from about 1% to about 30%, by weight, based on the total weight of the composition, and wherein the blend of two or more plant derived butters is present in an amount from at least about 20% to about 30%, by weight, based on the total weight of the composition.

In some embodiments, the at least one plant derived butter is selected from the group consisting of shea butter, cacao butter, murumuru butter, cupuacu butter, mango butter, and combinations thereof.

In some embodiments, the at least one plant derived butter comprises one or more of shea butter having a melting point that is in the range from about 45° C. to about 51° C. and present in an amount from about 1% to about 30%, by weight, based on the total weight of the composition, shea butter having a melting point that is in the range from about 30° C. to about 35° C. and present in an amount from about 1% to about 30%, by weight, based on the total weight of the composition, cacao butter present in an amount from about 1% to about 30%, by weight, based on the total weight of the composition, murumuru butter present in an amount from about 1% to about 30%, by weight, based on the total weight of the composition, cupuacu butter present in an amount from about 1% to about 30%, by weight, based on the total weight of the composition, and mango butter present in an amount from about 1% to about 30%, by weight, based on the total weight of the composition.

In some embodiments, the blend of structuring waxes is present in the composition in an amount from about 1.5% to about 20%, by weight, based on the total weight of the composition.

In some embodiments, the at least one nature derived wax in the blend of structuring waxes comprises rice bran wax, present in the composition in an amount that is from at least about 0.75%, by weight, based on the total weight of the composition.

In some embodiments, rice bran wax is present in the composition in an amount that is from about 0.75% to about 10%, by weight, based on the total weight of the composition, and wherein hydrogenated vegetable oil is present in the composition in an amount that is from about 0.75% to about 10%, by weight, based on the total weight of the composition.

In some embodiments, the glyceryl dibehenate, tribehenin and glyceryl behenate, in combination, is present in an amount from about 1.5% to about 20%, by weight, based on the total weight of the composition, and wherein each of glyceryl dibehenate, tribehenin and glyceryl behenate, individually, is present in an amount from about 0.5% to about 3%, by weight, based on the total weight of the composition.

In some embodiments, the glyceryl dibehenate, tribehenin and glyceryl behenate, in combination, is present in the blend of fatty compounds an amount from about 3% to about 6%, by weight, based on the total weight of the composition.

In some embodiments, the two or more fatty compounds selected from triglycerides and plant derived oils having a chain length from and including C8 to C24 in the blend of fatty compounds comprises two or more fatty compounds selected from caprylic-capric triglycerides, C10-C18 triglycerides, *Helianthus annuus* (sunflower) seed oil, *Glycine soja* (soybean) oil, and coco-caprylate/caprate.

In some embodiments, the blend of fatty compounds comprises caprylic-capric triglycerides, C10-C18 triglycerides, *Helianthus annuus* (sunflower) seed oil, *Glycine soja* (soybean) oil, and coco-caprylate/caprate, the blend present in the composition in a total amount from about 40% to about 50%, by weight, based on the total weight of the composition.

In some embodiments, the surfactant comprising glyceryl stearate is present in the composition in an amount from about 2% to about 20%, by weight, based on the total weight of the composition.

In some embodiments, the hydrating cosmetic composition comprises one or more of citric acid, tocopherol, and fragrance.

In some embodiments, the hydrating cosmetic composition is essentially free of one or more of paraffin waxes, ozokerite, petroleum derived compounds such as petrolatum, synthetic surfactants comprising polglyceryl esters of fatty acids, mineral oil and lanolin.

In some embodiments, the hydrating cosmetic composition is essentially free of hydrogenated polyisobutene and PEG-30 dipolyhydroxystearate.

In accordance with another embodiment, a hydrating cosmetic composition for keratinous substrates is provided, comprising: a stabilized anhydrous balm comprising:
 a) at least one glycol humectant present in an amount from at least about 10%, by weight, based on the total weight of the composition, the glycol humectant dispersed in a stabilized anhydrous fatty phase; and
 b) a stabilized anhydrous fatty phase comprising:
  i) at least one plant derived butter, wherein the at least one plant derived butter comprises one or more of shea butter having a melting point that is in the range from about 45° C. to about 51° C. and present in an amount from about 1% to about 30%, by weight, based on the total weight of the composition, shea butter having a melting point that is in the range from about 30° C. to about 35° C. and present in an amount from about 1% to about 30%, by weight, based on the total weight of the composition cacao butter present in an amount from about 1% to about 30%, by weight, based on the total weight of the composition, murumuru butter present in an amount from about 1% to about 30%, by weight, based on the total weight of the composition, cupuacu butter present in an amount from about 1% to about 30%, by weight, based on the total weight of the composition, and mango butter present in an amount from about 1% to about 30%, by weight, based on the total weight of the composition;
  ii) a blend of structuring waxes comprising at least one nature derived wax and hydrogenated vegetable oil, the structuring waxes present in a ratio of nature derived wax to hydrogenated vegetable oil in a range from about 3:1 to about 1:3, wherein the at least one nature derived wax in the blend of structuring waxes comprises rice bran wax, present in the composition in an amount that is from at least about 0.75%, by weight, based on the total weight of the composition, and wherein hydrogenated vegetable oil is present in the composition in an amount that is from about 0.75% to not more than about 3%, by weight, based on the total weight of the composition;
  iii) a blend of fatty compounds comprising glyceryl dibehenate, tribehenin and glyceryl behenate, and two or more fatty compounds selected from triglycerides and plant derived oils having a chain length from and including C8 to C24, the blend of fatty compounds, in combination, present in the composition in an amount from about 10% to about 50%, by weight, based on the total weight of the composition; and
  iv) a surfactant comprising glyceryl stearate,
  wherein the stabilized anhydrous balm is characterized as being stabilized as demonstrated by an absence of one or more of visible droplets and visible crystals after about eight weeks at 45° C.

In accordance with another embodiment, a method of forming a hydrating cosmetic composition for keratinous substrates is provided, comprising:
 c) at least one glycol humectant present in an amount from at least about 10%, by weight, based on the total weight of the composition, the glycol humectant dispersed in a stabilized anhydrous fatty phase; and
 d) a stabilized anhydrous fatty phase comprising:
  i) at least one plant derived butter, wherein the at least one plant derived butter comprises one or more of shea butter having a melting point that is in the range from about 45° C. to about 51° C. and present in an amount from about 1% to about 30%, by weight, based on the total weight of the composition, shea butter having a melting point that is in the range from about 30° C. to about 35° C. and present in an amount from about 1% to about 30%, by weight, based on the total weight of the composition cacao butter present in an amount from about 1% to about 30%, by weight, based on the total weight of the composition, murumuru butter present in an amount from about 1% to about 30%, by weight, based on the total weight of the composition, cupuacu butter present in an amount from about 1% to about 30%, by weight, based on the total weight of the composition, and mango butter present in an amount from about 1% to about 30%, by weight, based on the total weight of the composition, and wherein the at least one plant derived butter is present in a total amount from at least about 20%, by weight, based on the total weight of the composition;

ii) a blend of structuring waxes comprising at least one nature derived wax and hydrogenated vegetable oil, the structuring waxes are present in a ratio of hydrogenated vegetable oil to nature derived wax in a range from about 3:1 to about 1:3, wherein the at least one nature derived wax in the blend of structuring waxes comprises rice bran wax present in the composition in an amount that is from about 0.75% to about 10%, by weight, based on the total weight of the composition, and wherein hydrogenated vegetable oil is present in the composition in an amount that is from about 0.75% to about 10%, by weight, based on the total weight of the composition;

iii) a blend of fatty compounds comprising glyceryl dibehenate, tribehenin and glyceryl behenate, and two or more fatty compounds selected from triglycerides and fatty plant derived oils having a chain length from and including C8 to C24, wherein the glyceryl dibehenate, tribehenin and glyceryl behenate, in combination, is present in an amount from about 1.5% to about 20%, by weight, based on the total weight of the composition, and wherein each of glyceryl dibehenate, tribehenin and glyceryl behenate, individually, is present in an amount from about 0.5% to about 3%, by weight, based on the total weight of the composition, and wherein the blend of fatty compounds comprises caprylic-capric triglycerides, C10-C18 triglycerides, *Helianthus annuus* (sunflower) seed oil, *Glycine soja* (soybean) oil, and coco-caprylate/caprate, the blend present in the composition in a total amount from about 40% to about 50%, by weight, based on the total weight of the composition; and iv) a surfactant comprising glyceryl stearate present in the composition in an amount from about 2% to about 20%, by weight, based on the total weight of the composition, wherein the stabilized anhydrous balm is characterized as being stabilized as demonstrated by an absence of one or more of visible droplets and visible crystals after about eight weeks at 45° C., and wherein the composition is essentially free of one or more of paraffin waxes, ozokerite, petroleum derived compounds such as petrolatum, synthetic surfactants comprising polglyceryl esters of fatty acids, mineral oil and lanolin.

In accordance with another embodiment, a method of forming a hydrating cosmetic composition for keratinous substrates is provided, comprising the steps of (1) providing:

a) at least one glycol humectant present in an amount from at least about 10%, by weight, based on the total weight of the composition, and b) fatty phase components comprising:

i) at least one plant derived butter present in an amount from at least about 20%, by weight, based on the total weight of the composition;

ii) a blend of structuring waxes comprising at least one nature derived wax and hydrogenated vegetable oil, the structuring waxes present in a ratio of nature derived wax to hydrogenated vegetable oil in a range from about 3:1 to about 1:3;

iii) a blend of fatty compounds comprising glyceryl dibehenate, tribehenin and glyceryl behenate, and two or more fatty compounds selected from triglycerides and plant derived oils having a chain length from and including C8 to C24, the blend of fatty compounds, in combination, present in the composition in an amount from about 10% to about 50%, by weight, based on the total weight of the composition; and iv) a surfactant comprising glyceryl stearate;

(2) blending the components at a temperature that is greater than 55° C.;

(3) cooling the temperature prior to pouring to solidify, the pouring temperature less than about 55° C. and in range from about 35° C.

Other features and advantages of the present invention will be apparent from the following more detailed description, by way of example, the principles of the invention.

This disclosure describes particular embodiments in accordance with the general inventive concepts and is not intended to limit the scope of the invention in any way. Indeed, the invention as described in the specification is broader than and unlimited by the particular embodiments set forth herein, and the terms used herein have their full ordinary meaning.

DETAILED DESCRIPTION OF THE INVENTION

The term "anhydrous" as used herein means that a composition is anhydrous in that water has not been added as a component. In some embodiments, a composition is devoid of water. Those of skill in the art will appreciate that water may be present in a composition via one or more of its presence in the formulation components, processing conditions and absorption from the atmosphere; thus, in some embodiments a composition may be "essentially anhydrous" wherein water is present at a concentration that does not exceed 5% by weight, and more preferably not more than 1% by weight, based on the weight of the composition.

The terms "petrolatum-free" and "mineral oil-free" etc., as used herein mean that a composition lacks one or more of or is devoid of a component such as one or more of paraffin waxes, ozokerite, petroleum derived compounds such as petrolatum, synthetic surfactants comprising polglyceryl esters of fatty acids, mineral oil and lanolin. Those of skill in the art will appreciate that one or more of paraffin waxes, ozokerite, petroleum derived compounds such as petrolatum, synthetic surfactants comprising polglyceryl esters of fatty acids, mineral oil and lanolin may be present in a composition via one or more of its presence in the formulation components and processing condition. Accordingly, in some embodiments, a composition may be "essentially free" from one or more of paraffin waxes, ozokerite, petroleum derived compounds such as petrolatum, synthetic surfactants comprising polglyceryl esters of fatty acids, mineral oil and lanolin, wherein one or more of paraffin waxes, ozokerite, petroleum derived compounds such as petrolatum, synthetic surfactants comprising polglyceryl esters of fatty acids, mineral oil and lanolin is present at a concentration that does not exceed 5% by weight, and more preferably not more than 1% by weight, based on the weight of the composition. In some embodiments, one or more of paraffin waxes, ozokerite, petroleum derived compounds such as petrolatum, synthetic surfactants comprising polglyceryl esters of fatty acids, mineral oil and lanolin has not been added as a component in the composition. In some embodiments, a composition is devoid of one or more of paraffin waxes, ozokerite, petroleum derived compounds such as petrolatum, synthetic surfactants comprising polglyceryl esters of fatty acids, mineral oil and lanolin.

The term "plant derived butter" as used herein means a fat that is solid at room temperature (about 25° C.). A plant butter, often also referred to as a "vegetable butter," is a butter derived from a natural plant source.

The term "nature derived wax" as used herein means being intimately derived from natural sources such as living plants and animals.

The term "plant derived oils" as used herein means fatty plant derived oils that contain one or more fatty chain, and in some embodiments the fatty chain has a chain length from and including C8 to C24. Thus, in some embodiments, a fatty derived plant oil may comprise one or a blend of oils having a chain length of C8, C9, C10, C11, C12, C13, C14, C15, C16, C17, C18, C19, C20, C21, C22, C23, and C24.

The term "stabilized" as used herein with respect to an embodiment of an inventive composition means that the composition demonstrates an absence of visible droplets and crystals after about eight weeks at 45° C. The term "stability score" refers to a score in the range from 1-3 wherein a score of "1" means that the composition fails due to the presence of one or more of visible droplets and crystals at any time up to and including about eight weeks at 45° C. In some embodiments, a composition may be deemed to pass or fail with respect to stability though it may initially demonstrate desirable aesthetic properties. Thus, generally a score of "2" means that the composition is questionably acceptable and, thus, fails due to the presence of one or more of visible droplets and crystals. And a score of "3" means the composition passes for essentially lacking or being devoid of visible droplets and crystals after about eight weeks at 45° C.

The term "triglycerides" as used herein means one or more of caprylic/capric triglyceride, and triglycerides having a chain length from and including C10 to C18. Thus, in some embodiments, triglycerides may comprise one or a blend of triglycerides having a chain length of C10, C11, C12, C13, C14, C15, C16, C17, and C18.

The composition provides the surprising and unexpected benefits of a unique texture that provides a cushiony, creamy feel, especially noticeable upon pickup and initial application with a pleasing play time and a less oily feel during application. The textural benefits are achieved and by inclusion of a high humectant content together with a blend of structuring waxes and a balance of oil and butter components. In comparison to a comparative composition that lacks the humectant and waxes, the inventive composition demonstrates a richer, denser, more buttery texture, pickup and feel on skin and is stable.

Humectant

In accordance with the disclosure, one or more humectants are present in the composition. Non-limiting examples of humectants include glycerin, squalane, sucrose, triacetin, monoethylene glycol, diethylene glycol, triethylene glycol, propylene glycol, butylene glycol, dipropylene glycol, diethylene glycol, hexylene glycol, glycol ethers such as monopropylene, dipropylene and tripropylene glycol alkyl($C_1$-$C_4$) ethers, glycerol, xylitol, maltitol, sorbitol, pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract.

In some embodiments, the hydrating agent comprises a glycol humectant, and in some particular embodiments, the hydrating agent that comprises a glycol humectant comprises glycerin.

In accordance with the various embodiments, the one or more humectants is present in a composition in the range from about 10% to about 25%, or from about 10% to about 20%, or from about 10% to about 15%, or any suitable combination, sub-combination, range, or sub-range thereof by weight, based on the weight of the composition. In some embodiments, the one or more humectants is present from at least 10%, or from at least 12%, or from at least 15%, by weight, based on the total weight of the composition.

Thus, one or a combination of humectants may be present, by weight, based on the total weight of the composition, each one present from about 1, 2, 3, 4, 5, 6, 7, 8, 9, 10, 11, 12, 13, 14, 15, 16, 17, 18, 19, 20, 21, 22, 23, 24 to about 25 weight percent, including increments and ranges therein and there between, and a combination of humectants is present in total in an amount from about 10, 11, 12, 13, 14, 15, 16, 17, 18, 19, 20, 21, 22, 23, 24 to about 25 weight percent, including increments and ranges therein and there between.

Anhydrous Fatty Phase

Plant Derived Butter

In accordance with the disclosure, at least one plant derived butter is present in the hydrating cosmetic composition. In accordance with some embodiments, the plant butters are selected from fats having a hydrocarbon chain distribution of C12:30-55%/C14:10-40% wherein the fat has two hydrocarbon chains, one hydrocarbon chain having 12 carbons and being present in the fat in an amount from 30-55%, and a second hydrocarbon chain having 14 carbons and being present in the fat from 10-40%, for example murumuru seed butter and babassu butter. In some embodiments, the plant butters are selected from shea butter, cacao butter, murumuru butter, cupuacu butter, mango butter, orange wax and combinations thereof.

In accordance with some embodiments, the hydrating cosmetic composition comprises at least two plant butters, and more than two plant butters. In some embodiments, the hydrating cosmetic composition includes a combination of plant butters that differ in at least one property, for example melting point. In one example, the hydrating cosmetic composition includes a combination of plant butters wherein at least one plant butter has a melting point that is in the range from about 45° C. to about 51° C., and at least one other plant butter has a melting point that is in the range from about 30° C. to about 35° C., wherein the plant butters having differing melting points may be from the same plant origin, for example they may both be shea butters, or from different plant origins. According to such embodiments, the plant butters may be present in a ratio by weight of from 1:10 to 10:1. Of course, it will be appreciated that in various embodiments, a blend of the same generic form of a plant butter, such as but not limited to shea butter, may be combined wherein each of the plant butters of that form has a different meeting point, and in some embodiments only a single form of a plant butter may be selected.

In one embodiment, the hydrating cosmetic composition comprises each of shea butter, cacao butter, murumuru butter, cupuacu butter, and mango butter. In a particular example of such an embodiment, the shea butter component of the hydrating cosmetic composition comprises one or more of shea butter having a melting point that is in the range from about 45° C. to about 51° C. and present in an amount from about 1% to about 30%, by weight, based on the total weight of the composition, and shea butter having a melting point that is in the range from about 30° C. to about 35° C. and present in an amount from about 1% to about 30%, by weight, based on the total weight of the composition, together with cacao butter present in an amount from about 1% to about 30%, by weight, based on the total weight of the composition, murumuru butter present in an amount from about 1% to about 30%, by weight, based on the total weight of the composition, cupuacu butter present in an amount from about 1% to about 30%, by weight, based on the total weight of the composition, and mango butter present in an amount from about 1% to about 30%, by weight, based on the total weight of the composition. In a further particular embodiment, the hydrating cosmetic composition comprises shea butter having a melting point that is in the range from about 45° C. to about 51° C., and shea butter having a melting point that is in the range from about 30° C. to about 35° C., wherein two shea butters present in a ratio by weight of from 6:1.

In accordance with the various embodiments, each one of the at least one plant derived butter is present in a composition in the range from about 1% to about 30%, or from about 1% to about 20%, or from about 1% to about 5%, or from about 5% to about 10%, or from about 1.5% to about 6%, or from about 2% to about 4%, or from about 3.5% to about 6% or any suitable combination, sub-combination, range, or sub-range thereof by weight, based on the weight of the composition. In some embodiments, each one of the at least one plant derived butter is present from at least about 1%, or from at least about 5%, or from at least about 6% and up to about 5%, or up to about 10%%, by weight, based on the total weight of the composition.

Thus, one or a combination of plant derived butters may be present, by weight, based on the total weight of the composition, each one present from about 1, 2, 3, 4, 5, 6, 7, 8, 9, 10, 11, 12, 13, 14, 15, 16, 17, 18, 19, 20, 21, 22, 23, 24, 35, 26, 27, 28, 29 to about 30 weight percent, including increments and ranges therein and there between, and a combination of plant derived butters is present in total in an amount from at least about 20, 21, 22, 23, 24, 25, 26, 27, 28, 29 to about 30 weight percent, including increments and ranges therein and there between.

Blend of Structuring Waxes

In accordance with the disclosure, a blend of structuring waxes comprising at least one nature derived wax and hydrogenated vegetable oil is present in the hydrating cosmetic composition.

Natural waxes can include rice bran wax, bayberry wax, beeswax, grapefruit wax, orange peel wax, palm wax, sumac wax, sunflower wax, soy wax, and combinations thereof.

Hydrogenated vegetable oil can include totally or partially hydrogenated plant oils, for instance hydrogenated soybean oil, hydrogenated coconut oil, hydrogenated rapeseed oil, mixtures of hydrogenated plant oils such as the mixture of hydrogenated soybean, coconut, palm and rapeseed plant oil, trans-isomerized partially hydrogenated jojoba oil, and partially hydrogenated olive oil.

In accordance with the various embodiments, each of at least one nature derived wax and hydrogenated vegetable oil is present in the hydrating cosmetic composition at a concentration, by weight, of between about 0.25% to about 10%, based on the total weight of the hydrating cosmetic composition. In accordance with the various embodiments, each of at least one nature derived wax and hydrogenated vegetable oil is present in the hydrating cosmetic composition at a concentration, by weight, of from about 0.25% to about 10%, or from about 0.75% to about 5%, or from about 1.25% to about 3%, or from about 1.5% to about 2.25%, or any suitable combination, sub-combination, range, or sub-range thereof by weight, based on the weight of the composition.

In the various embodiments, the at least one nature derived and the hydrogenated vegetable oil are present in a ratio of nature derived wax to hydrogenated vegetable oil in a range from about 4:1 to about 1:3, or from about 3:1 to about 1:3, or about 1:1.

In some embodiments, the at least one nature derived wax in the blend of structuring waxes is present in the composition in an amount that is from about 0.75% to about 10%, by weight, based on the total weight of the composition, and the hydrogenated vegetable oil is present in the composition in an amount that is from about 0.75% to about 10%, by weight, based on the total weight of the composition.

In some embodiments, the blend of structuring waxes is present in the composition in an amount from about 1.5% to about 20%, by weight, based on the total weight of the composition.

In some embodiments, the at least one nature derived wax in the blend of structuring waxes is present in the composition in an amount that is from at least about 0.75%, by weight, based on the total weight of the composition.

In some embodiments, the at least one nature derived wax in the blend of structuring waxes comprises rice bran wax, present in the composition in an amount that is from at least about 0.75%, by weight, based on the total weight of the composition, and the hydrogenated vegetable oil is present in the composition in an amount that is from about 0.75% to not more than about 3%, by weight, based on the total weight of the composition.

Thus, the blend structuring waxes is present, by weight, based on the total weight of the composition, each one or the combination from about 0.25, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

Blend of Fatty Compounds

In accordance with the disclosure, provided are compositions that comprise a blend of fatty compounds that include an emollient blend comprising glyceryl dibehenate, tribehenin and glyceryl behenate, and two or more fatty compounds selected from triglycerides and plant derived oils having a chain length from and including C8 to C24.

In accordance with the various embodiments, the emollient blend comprises the raw materials comprising glyceryl dibehenate, tribehenin and glyceryl behenate, each, alone or as blended, may be provided in a solvent. In some embodiments, the emollient blend comprises glyceryl dibehenate, tribehenin and glyceryl behenate present, at a ratio of about 1:1:1, or at a ratio of about 3:2:1 by weight, based on the weight of the emollient blend.

As used herein, glyceryl dibehenate is used to refer to the compound that is alternately identified in the art as 2-Hydroxypropane-1,3-diyl didocosanoate; Docosanoic acid, 1,1'-(2-hydroxy-1,3-propanediyl) ester; 1,3-dibehenin; 1-Behenoyl-3-behenoyl-sn-glycerol; 1,2,3-Propanetriol 1,3-dibehenate; 1-Docosanoyl-3-docosanoyl-sn-glycerol; and Diacylglycerol (22:0/0:0/22:0). As used herein, Tribehenin is used to refer to the compound that is alternately identified in the art as 2,3-propanetriyl ester behenic acid; 1,2,3-propanetriyl ester docosanoic acid; 1,2,3-propenetriol tridocosanoate; behenic acid, 1,2,3-propanetriyl ester; docosanoic acid, 1,2,3-propanetriyl ester; docosanoic acid, 1,2,3propanetriyl ester; glyceryl tribehenate; propane-1,2,3-triyl tridocosanoate; compritol 888; and docosanoin, tri-(7ci,8ci). And, as used herein, glyceryl behenate is used to refer to the compound that is alternately identified in the art as 2,3-dihydroxypropyl docosanoate; 2,3-dihydroxypropyl ester docosanoic acid; behenic acid monoglyceride; docodanoin, mono-; docosanoic acid, 2,3-dihydroxypropyl ester; docosanoic acid, monoester with 1,2,3-propanetriol; glycerin monobehenate; glycerol monobhenate; glyceryl monobehenate; mono-docodanoin; and monoester with 1,2,3-propanetriol docodanoic acid.

In accordance with the various embodiments, the emollient blend is present in the composition together with one or more surfactant comprising glyceryl stearate, the combination being present in the composition at a concentration up to and including about 30% by weight, based on the weight of the hydrating cosmetic composition. In some embodiments, the combination is present in the range from about 1% to about 30%, or from about 1% to about 25%, or from about 1% to about 10%, or from about 1% to about 7%, or from about 2% to about 6%, or from about 3% to about 5%, or from about 5% to about 15%, or from about 6% to about 10%, or any suitable combination, sub-combination, range, or sub-range thereof by weight, based on the weight of the composition.

In accordance with the various embodiments, the surfactant may be present in the hydrating cosmetic composition in a ratio of the surfactant to emollient blend of from about 2:1 to about 1:2, by weight, based on the weight of the hydrating cosmetic composition. Thus, in some embodiments, the one or more surfactant comprising glyceryl stearate and the emollient blend may be present at a ratio of 1:1, by weight, based on the weight of the hydrating cosmetic composition.

In accordance with the various embodiments, the emollient blend is present in the hydrating cosmetic composition at a concentration, by weight, of at least about 2%, based on the total weight of the hydrating cosmetic composition.

In accordance with the various embodiments, the emollient blend is present in the hydrating cosmetic composition at a concentration, by weight, based on the total weight of the hydrating cosmetic composition, in the range from about 0.01% to about 20%, or from about 2% to about 20%, or from about 0.05% to about 10%, or from about 0.1% to about 4%, or from about 0.1% to about 3.5%, or from about 0.7% to about 1.5%, or from about 3.5% to about 5%, or any suitable combination, sub-combination, range, or sub-range thereof by weight, based on the weight of the composition.

Thus, the emollient blend is present, by weight, based on the total weight of the composition, each one or the combination present from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19 to about 20 weight percent, including increments and ranges therein and there between.

More particularly, each one of glyceryl dibehenate, tribehenin and glyceryl behenate is present in the hydrating cosmetic composition at a concentration, by weight, based on the total eight of the hydrating cosmetic composition, in the range from about 0.01% to about 20%, or from about 2% to about 20%, or from about 0.05% to about 10%, or from about 0.1% to about 4%, or from about 0.1% to about 3.5%, or from about 0.7% to about 1.5%, or from about 3.5% to about 5%, or any suitable combination, sub-combination, range, or sub-range thereof, by weight, based on the weight of the composition.

Thus, each one of glyceryl dibehenate, tribehenin and glyceryl behenate is present, by weight, based on the total weight, from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19 to about 20 weight percent, including increments and ranges therein and there between.

Fatty Compounds

In accordance with the disclosure, a blend of fatty compounds is present in the hydrating cosmetic composition, the blend of fatty compounds including one or more additional oils selected from fatty plant derived oils that comprises one or more fatty chain having a chain length from and including C8 to C24. In accordance with some embodiments, the fatty compounds are selected from one or more of *Helianthus annuus* (sunflower) seed oil, *Glycine soja* (soybean) oil, coco-caprylate/caprate, *Ricinus communis* (castor) seed oil, *Prunus amygdalus dulcis* (sweet almond) oil, and *Prunus armeniaca* (apricot) kernel oil. In accordance with some embodiments, the two or more fatty compounds includes more than two fatty compounds.

In a particular embodiment, the two or more fatty compounds includes each of *Helianthus annuus* (sunflower) seed oil, *Glycine soja* (soybean) oil, and coco-caprylate/caprate.

In accordance with some embodiments, the two or more fatty compounds is present in the hydrating cosmetic composition at a concentration, by weight, of at least about 10%, based on the total weight of the hydrating cosmetic composition. In accordance with the various embodiments, the two or more fatty compounds is present in the hydrating cosmetic composition at a concentration, by weight, of from about 10% to about 50%, or from about 15% to about 45%, or from about 20% to about 40%, or from about 25% to about 35%, or any suitable combination, sub-combination, range, or sub-range thereof by weight, based on the weight of the composition.

Thus, in some embodiments, the two or more fatty compounds is present, by weight, based on the total weight of the composition, from about at least 10, 11, 12, 13, 14, 15, 16, 17, 18, 19, 20, 21, 22, 23 24, 25, 26, 27, 28, 29, 30, 31, 32, 22, 34 35 36, 37, 38, 39, 40, 41, 42, 43, 44, 45, 46, 47, 48, 49 to about 50 weight percent, including increments and ranges therein and there between.

In accordance with the various embodiments, each one of the two or more fatty compounds is present in the hydrating cosmetic composition at a concentration, by weight, based on the total weight of the hydrating cosmetic composition, in the range from about 0.1% to about 50%, or from about 0.5% to about 50%, or from about 1% to about 20%, or from about 2% to about 20%, or from about 1.5% to about 15%, or from about 1.5% to about 10%, or from about 1.5% to about 5%, or from about 1.5% to about 2.5%, or from about 2.5% to about 5%, or from about 4% to about 10%, or any suitable combination, sub-combination, range, or sub-range thereof by weight, based on the weight of the composition.

Thus, each one of the two or more fatty compounds is present, by weight, based on the total weight of the composition, each one or the combination present from about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 22, 34 35 36, 37, 38, 39, 40, 41, 42, 43, 44, 45, 46, 47, 48, 49 to about 50 weight percent, including increments and ranges therein and there between.

Triglycerides

In accordance with the disclosure, one or more triglycerides may be present in the two or more fatty compounds in the blend of fatty compounds in the hydrating cosmetic composition. Triglycerides can include caprylic/capric triglyceride, triglycerides having a chain length from and including C10 to C18, and combinations thereof. Examples of C10 to C18 triglycerides include, for example, C10 triglyceride, C11 triglyceride, etc.

In a particular embodiment, the one or more triglyceride includes caprylic/capric triglyceride together with one or more triglycerides having a chain length from and including C10 to C18.

In accordance with the various embodiments, the one or more triglycerides is present in the hydrating cosmetic composition at a concentration, by weight, of between about 2% to about 50%, based on the total weight of the hydrating cosmetic composition. In accordance with the various embodiments, the one or more triglycerides is present in the hydrating cosmetic composition at a concentration, by weight, of from about 2% to about 50%, or from about 2% to about 40%, or from about 10% to about 40%, or from about 20% to about 35%, or from about 22% to about 35%, or from about 25% to about 35%, or from about 25% to about 45%, or from about 30% to about 45%, or any suitable combination, sub-combination, range, or sub-range thereof by weight, based on the weight of the composition.

In some embodiments, the composition comprises a plurality of triglycerides, the combination of which is present at a concentration, by weight, of between about 20% to about 50%, based on the total weight of the hydrating cosmetic composition. In accordance with such embodiments, each one of the plurality of triglycerides is present in the hydrating cosmetic composition at a concentration, by weight, based on the total weight of the hydrating cosmetic composition, in the range from about 1% to about 40%, or from about 12% to about 40%, or from about 3% to about 30%, or from about 3% to about 10%, or from about 5% to about 35%, or from about 10% to about 30%, or any suitable combination, sub-combination, range, or sub-range thereof by weight, based on the weight of the composition.

Thus, each one of or the combination of triglycerides is present, by weight, based on the total weight of the composition, each one or the combination present from about 1, 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 22, 34 35 36, 37, 38, 39, 40, 41, 42, 43, 44, 45, 46, 47, 48, 49 to about 50 weight percent, including increments and ranges therein and there between.

Surfactant

In accordance with the disclosure, the composition includes one or more surfactant comprising glyceryl stearate. In some embodiments, the one or more surfactant may further comprise potassium stearate and/or sodium stearate. The composition may include other stearate-based surfactant compounds.

As used herein, glyceryl stearate is used to refer to the compound that is alternately identified in the art as octadecanoic acid, ester with 1,2,3 propanetriol; self-emulsifying glyceryl monostearate; and stearine.

In accordance with the various embodiments, the one or more surfactant comprising glyceryl stearate is present in the hydrating cosmetic composition at a concentration ranging from about 0.01% to about 20%, by weight relative to the weight of the composition, or from about 2% to about 20%, or from about 0.1% to about 15%, or from about 0.1% to about 5% by weight, or from about 0.15% to about 4% by weight, or from about 0.5% to about 3.5%, or from about 0.75 to about 1.25%, or any suitable combination, sub-combination, range, or sub-range thereof by weight, based on the weight of the composition. In some embodiments, the one or more surfactant comprising glyceryl stearate is present from at least 1%, or from at least 2%. In some embodiments, one or more additional surfactants can be present in the hydrating cosmetic composition according to the disclosure.

Thus, the one or more surfactant comprising glyceryl stearate is present, alone or in combination with another surfactant, by weight, based on the total weight of the composition, each one or the combination present from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

Solvent

In accordance with the disclosure, one or more solvents may be present in the hydrating cosmetic composition. In accordance with some embodiments, the composition includes one or more solvents comprising a glycol. Glycols may be selected from and include, by way of nonlimiting examples, glycerin, caprylyl glycol, propylene glycol, propanediol, polyethylene glycol, and other glycols, and combinations of these. In some particular embodiments, the one or more solvents comprises propanediol.

In accordance with the various embodiments, the amount of the one or more solvents that may be present in the hydrating cosmetic composition ranges from about 0.1% to about 20%, or of from about 0.1% to about 15%, or from about 0.1% to about 10%, or from about 0.1% to about 5%, or from about 0.2% to about 4%, or from about 0.3% to about 3%, or any suitable combination, sub-combination, range, or sub-range thereof by weight, based on the weight of the composition.

Thus, one or a combination of solvents may be present, by weight, based on the total weight of the composition, each one or the combination present from about 0.10, 0.20, 0.30, 0.40, 0.50, 0.60, 0.70, 0.80, 0.90, 1, 2, 3, 4, 5, 6, 7, 8, 9, 10, 11, 12, 13, 14, 15, 16, 17, 18, 19 to about 20 weight percent, including increments and ranges therein and there between.

Water

In accordance with the various embodiments, the compositions are essentially anhydrous or are devoid of water.

Chelating Agents

In accordance with the disclosure, in some embodiments, one or more other components comprising chelating agents can be present in the hydrating cosmetic composition according to the disclosure. In some particular embodiments, chelating agents are selected from sodium phytate, ethylenediaminetetraacetic acid (EDTA), tetrasodium etidronate, tetrasodium pyrophosphate, pentasodium ethylenediamine tetramethylene phosphonate, sodium staminate and combinations of these. In some particular embodiments, chelating agents comprise sodium phytate.

In accordance with the various embodiments, the amount of chelating agents present in the hydrating cosmetic composition can be present in the hydrating cosmetic composition according to the disclosure in a range from about 0.01% to about 5% by weight, or from about 0.05% to about 2% by weight, or from about 0.10% to about 1%, or from about 0.15% to about 0.5%, and from about 0.15% to about 0.2%, or any suitable combination, sub-combination, range, or sub-range thereof by weight, based on the weight of the composition.

Thus, one or a combination of chelating agents may be present, by weight, based on the total weight, each one or the combination present from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2.0, 3.0, 4.0 up to about 5.0 weight percent, including increments and ranges therein and there between.

Actives

In accordance with the disclosure, in some embodiments, there may be one or more actives present in the cosmetic composition. In some embodiments, actives used according to the disclosure may be selected from; anti-microbial components, including, but not limited to, sodium salicylate; antioxidants, including, but not limited to, phenolic compounds, such as chalcones, flavones, flavanones, flavanols, dihydroflavonols, isoflavonoids, neoflavonoids, catechins, anthocyanidins, tannins, lignans, aurones, stilbenoids, curcuminoids, alkylphenol s, betacyanins, capsacinoids, hydroxybenzoketones, methoxyphenols, naphthoquinones, phenolic terpenes, resveratrol, curcumin, pinoresinol, ferulic acid, hydroxytyrosol, cinnamic acid, caffeic acid, p-coumaric acid, baicalin, pine bark extract, ellagic acid; and vitamins and vitamin derivatives, such as panthenol, tocopherol, ascorbic acid; and combinations thereof. Although the aforementioned optional active components are given as an example, it will be appreciated that other optional components compatible with cosmetic applications known in the art may be used.

In accordance with the various embodiments, the amount of one or more actives, alone or in combination, present in the hydrating cosmetic composition can be present in the composition according to the disclosure in a range from about 0.01% to about 20%, by weight, or from about 0.05% to about 15%, or from about 0.1% to about 10%, or from about 0.15% to about 5%, or from about 0.40% to about 4%, or from about 0.50% to about 2% by weight, or from about 1% to about 2%, or any suitable combination, sub-combination, range, or sub-range thereof by weight, based on the weight of the composition.

Thus, one or a combination of actives may be present, by weight, based on the total weight of the composition, each one or the combination present from about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

EXAMPLES

Example 1: Comparative and Inventive Compositions

Compositions according to the disclosure are formed by a heat-based blending process for combining the humectant components with the fatty components. According to the method for forming the inventive compositions, wherein stability as described herein is achieved, the components are blended at a temperature that is greater than 55° C. followed by cooling the temperature prior to pouring to solidify, the pouring temperature being less than about 55° C. and in range from about 35° C.

TABLE 1

Comparative and Inventive compositions

| INCI US | Comparative Formulation #1 | Exemplary Inventive Formulation |
|---|---|---|
| Glyceryl Dibehenate | 2.12 | 2.12 |
| Tribehenin | 1.2 | 1.2 |
| Glyceryl Behenate | 0.68 | 0.68 |
| Coco-Caprylate/Caprate | 10 | 10 |
| *Helianthus Annuus* Seed Oil | 11 | 11 |
| Caprylic/Capric Triglyceride | 15.7 | 15.65 |
| Glycerin | 15 | 15 |
| C10-18 Triglycerides | 10 | 10 |
| Tocopherol | 0.3 | 0.3 |
| *Oryza Sativa* Cera (Rice) Bran Wax | | 1 |
| Propanediol | 3 | 3 |
| Glyceryl Stearate | 4 | 4 |
| Hydrogenated Vegetable Oil | 3 | 1.25 |
| *Butyrospermum Parkii* Butter | 6 | 6 |
| *Theobroma Grandiflorum* Seed Butter | 3.5 | 3.5 |
| *Astrocaryum Murumuru* Seed Butter | 3.5 | 3.5 |
| *Butyrospermum Parkii* Butter | 10 | 10 |
| *Butyrospermum Parkii* Butter | 1 | 1 |
| Parfum | | 0.8 |

Example 2: Inventive and Comparative Testing

TABLE 2

Tactile Properties of Inventive and Comparative Compositions

| INCI US | Exemplary Inventive Formulation | Experimental Formulation #1 | Experimental Formulation #2 | Experimental Formulation #3 |
|---|---|---|---|---|
| Glyceryl Stearate | 4 | 4 | 4. | 4 |
| C10-18 Triglycerides | 10 | 10 | 10 | 10 |
| *Butyrospermum Parkii* (Shea) Butter | 10 | 10 | 10 | 10 |
| Propanediol | 3 | 3 | 3 | 3 |
| Hydrogenated Vegetable Oil | 1.25 | 1.25 | 1.25 | 1.25 |
| *Oryza Sativa* (Rice) Bran Wax | 1 | 1 | 1 | 1 |
| *Astrocaryum Murumuru* Seed Butter | 3.5 | 3.5 | 3.5 | 3.5 |
| Caprylic/Capric Triglyceride | 15.65 | 15.35 | 14.35 | 15.35 |
| Glyceryl Dibehenate (And) Tribehenin (And) Glyceryl Behenate | 4 | 4 | 4 | 4 |
| Glycerin | 15 | 15 | 15 | 15 |
| *Helianthus Annuus* | 11 | 18 | 10 | 13 |

TABLE 2-continued

Tactile Properties of Inventive and Comparative Compositions

| INCI US | Exemplary Inventive Formulation | Experimental Formulation #1 | Experimental Formulation #2 | Experimental Formulation #3 |
|---|---|---|---|---|
| (Sunflower) Seed Oil Coco-Caprylate/Caprate | 10 | 10 | 10 | 10 |
| *Butyrospermum Parkii* (Shea) Butter (melting point ~32-34° C.) | 1 | 1 | 10 | 1 |
| Tocopherol | 0.3 | 0.4 | 0.4 | 0.4 |
| *Theobroma Grandiflorum* Seed Butter | 3.5 | 3.5 | 3.5 | 3.5 |
| *Butyrospermum Parkii* (Shea) Butter (melting point ~51° C.) | 6 | | | 5 |
| PROPERTIES | Non greasy, rich, buttery texture. | Oily, fluid feel. | Oily/greasy feel with hard texture. | Non greasy, rich, buttery texture. |

Example 3: Stability Testing

TABLE 3

Base formulation for varying ratios of waxes

| INCI US | Base Formulation |
|---|---|
| Glyceryl Dibehenate (And) Tribehenin (And) Glyceryl Behenate | 4 |
| Coco-Caprylate/Caprate | 10 |
| *Helianthus Annuus* (Sunflower) Seed Oil | 11 |
| Caprylic/Capric Triglyceride | 15.65 (QS in Test) |
| Glycerin | 15 |
| C10-18 Triglycerides | 10 |
| Tocopherol | 0.3 |
| *Oryza Sativa* (Rice) Bran Wax | (Varied in Test) |
| Propanediol | 3 |
| Glyceryl Stearate | 4 |
| Hydrogenated Vegetable Oil | (Varied in Test) |
| *Butyrospermum Parkii* (Shea) Butter | 6 |
| *Theobroma Grandiflorum* Seed Butter | 3.5 |
| *Astrocaryum Murumuru* Seed Butter | 3.5 |
| *Butyrospermum Parkii* (Shea) Butter | 10 |
| *Butyrospermum Parkii* (Shea) Butter | 1 |
| Fragrance | 0.8 |

A panel of test formulations were prepared using a temperature-controlled blending process, the test formulations comprising the base formulation shown in Table 3 with varied ratio of the wax blend that included rice bran wax and hydrogenated vegetable. The compositions were subjected to stability testing and were evaluated for the presence of visible fluid droplet and/or crystal formation on the surface of the balm at selected intervals of time, and under conditions of exposure to freeze thaw and heating in the range from 4° C., to 25° C. to 45° C. Stability was scored between 1 and 3, the sore accounting for any formation of visible fluid droplet and/or crystal formation on the surface of the balm.

TABLE 4

Stability Test Results: varying ratios of waxes in Base Formulation

| Formula | Rice Bran Wax | Hydrogenated Vegetable OIL | Ratio | Stability Score |
|---|---|---|---|---|
| 1 | 0.75 | 0.75 | 1:1 | 3 |
| 2 | 2.25 | 0.75 | 3:1 | 3 |
| 3 | 0.75 | 2.25 | 1:3 | 2 |
| 4 | 0 | 1.5 | | 2 |
| 5 | 1.5 | 0 | | 3 |
| 6 | 1.5 | 1.5 | 1:1 | 3 |
| 7 | 3 | 0.75 | 4:1 | 3 |
| 8 | 1.5 | 2.25 | 1:2 | 2 |
| 9 | 0 | 0.75 | | 1 |
| 10 | 0 | 2.25 | | 1 |
| 11 | 2.25 | 0 | | 3 |
| 12 | 0.75 | 3 | 1:4 | 1 |
| 13 | 0.75 | 1.5 | 1:2 | 2 |
| 14 ** | 0 | 3 | | 1 |
| 15 | 0.75 | 0 | | 2 |

** (Comparative Formulation #1)

As shown by the data, stability was optimal when the plant derived wax, for example rice bran wax, is present in the base formulation in an amount greater than or equal to about 1.5% in the absence of hydrogenated vegetable oil. And stability was optimal (3) when the plant derived wax, for example rice bran wax, is present in the base formulation together with hydrogenated vegetable oil in respective amounts from about 0.75% to about 3% of rice bran wax, and from about 0.75% up to about 1.5% hydrogenated vegetable oil, the waxes present in a ratio of rice bran wax to hydrogenated vegetable oil in a range from 1:1 to 4:1. Stability is acceptable (2) when the hydrogenated vegetable oil is present at about 1.5% in the absence of plant derived wax, and when the plant derived wax, for example rice bran wax, is present in the base formulation in an amount as low as 0.75% in the absence of hydrogenated vegetable oil, and when the plant derived wax and the hydrogenated vegetable oil are present in a ratio of rice bran wax to hydrogenated vegetable oil in a range from 1:2 to 1:3. Formulations with a score of 1 are failed.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"One or more," as used herein, means at least one, and thus includes individual components as well as mixtures/combinations.

The transitional terms "comprising", "consisting essentially of" "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

While the invention has been described with reference to a preferred embodiment, it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention is not limited to the particular embodiment disclosed as the best mode contemplated for carrying out this invention, but that the invention will include all embodiments falling within the scope of the appended claims.

What is claimed is:

1. A hydrating cosmetic composition for keratinous substrates, consisting of:
   a stabilized anhydrous balm consisting of:
   a) at least one glycol humectant that includes glycerin, wherein the glycerin is present in an amount from at least about 10%, by weight, based on the total weight of the composition, the glycol humectant dispersed in a stabilized anhydrous fatty phase; and
   b) a stabilized anhydrous fatty phase that includes:
      i) at least one plant derived butter present in an amount from at least about 20%, by weight, based on the total weight of the composition;
      ii) a blend of structuring waxes that includes at least one nature derived wax and hydrogenated vegetable oil, the structuring waxes present in a ratio of nature derived wax to hydrogenated vegetable oil in a range from about 3:1 to about 1:3;
      iii) a blend of fatty compounds that includes glyceryl dibehenate, tribehenin and glyceryl behenate, with or without a solvent, and two or more fatty compounds selected from triglycerides and plant derived oils having a chain length from and including C8 to C24, the blend of fatty compounds, in combination, present in the composition in an amount from about 10% to about 50%, by weight, based on the total weight of the composition; and
      iv) a surfactant that includes glyceryl stearate; and
   c) optionally, one or more ingredients selected from the group consisting of chelating agents, anti-microbial components, antioxidants, vitamins, vitamin derivatives fragrances, and combinations thereof.

2. The hydrating cosmetic composition according to claim 1, wherein the stabilized anhydrous balm is characterized as being stabilized as demonstrated by an absence of visible droplets and crystals after about eight weeks at 45° C.

3. The hydrating cosmetic composition according to claim 1, wherein glycerin is present in the composition in an amount from at least about 10% and to about 25%, by weight, based on the total weight of the composition.

4. The hydrating cosmetic composition according to claim 3, wherein the at least one glycol humectant further includes a glycol solvent selected from the group consisting of propanediol, caprylyl glycol, polypropylene glycol, and combinations thereof.

5. The hydrating cosmetic composition according to claim 4, wherein the glycol solvent includes propanediol and is present in the composition in an amount from about 1% to about 10%, by weight, based on the total weight of the composition.

6. The hydrating cosmetic composition according to claim 1, wherein the at least one plant derived butter includes a blend of two or more plant derived butters, each plant derived butter present in an amount from about 1% to about 30%, by weight, based on the total weight of the composition, and wherein the blend of two or more plant derived butters is present in an amount from at least about 20% to about 30%, by weight, based on the total weight of the composition.

7. The hydrating cosmetic composition according to claim 1, wherein the at least one plant derived butter is selected from the group consisting of shea butter, cacao butter, murumuru butter, cupuacu butter, mango butter, and combinations thereof.

8. The hydrating cosmetic composition according to claim 7, wherein the at least one plant derived butter includes one or more of shea butter having a melting point that is in the range from about 45° C. to about 51° C. and present in an amount from about 1% to about 30%, by weight, based on the total weight of the composition, shea butter having a melting point that is in the range from about 30° C. to about 35° C. and present in an amount from about 1% to about 30%, by weight, based on the total weight of the composition, cacao butter present in an amount from about 1% to about 30%, by weight, based on the total weight of the composition, murumuru butter present in an amount from about 1% to about 30%, by weight, based on the total weight of the composition, cupuacu butter present in an amount from about 1% to about 30%, by weight, based on the total weight of the composition, and mango butter present in an amount from about 1% to about 30%, by weight, based on the total weight of the composition, and wherein the at least one plant derived butter is present in a total amount from at least about 20%, by weight, based on the total weight of the composition.

9. The hydrating cosmetic composition according to claim 1, wherein the blend of structuring waxes is present in the composition in an amount from about 1.5% to about 20%, by weight, based on the total weight of the composition.

10. The hydrating cosmetic composition according to claim 1, wherein the at least one nature derived wax in the blend of structuring waxes includes rice bran wax, present in the composition in an amount that is from at least about 0.75% and up to about 10%, by weight, based on the total weight of the composition.

11. The hydrating cosmetic composition according to claim 10, wherein rice bran wax is present in the composition in an amount that is from about 0.75% to about 10%, by weight, based on the total weight of the composition, and wherein hydrogenated vegetable oil is present in the composition in an amount that is from about 0.75% to about 10%, by weight, based on the total weight of the composition.

12. The hydrating cosmetic composition according to claim 1, wherein the glyceryl dibehenate, tribehenin and glyceryl behenate, in combination, is present in an amount from about 1.5% to about 20%, by weight, based on the total weight of the composition, and wherein each of glyceryl dibehenate, tribehenin and glyceryl behenate, individually, is present in an amount from about 0.5% to about 3%, by weight, based on the total weight of the composition.

13. The hydrating cosmetic composition according to claim 1, wherein the glyceryl dibehenate, tribehenin and glyceryl behenate, in combination, is present in the blend of fatty compounds an amount from about 3% to about 6%, by weight, based on the total weight of the composition.

14. The hydrating cosmetic composition according to claim 1, wherein the two or more fatty compounds selected from triglycerides and plant derived oils having a chain length from and including C8 to C24 in the blend of fatty compounds includes two or more fatty compounds selected from the group consisting of caprylic-capric triglycerides, C10-C18 triglycerides, sunflower seed oil, soybean oil, and coco-caprylate/caprate, and combinations thereof.

15. The hydrating cosmetic composition according to claim 1, wherein the blend of fatty compounds includes caprylic-capric triglycerides, C10-C18 triglycerides, sunflower seed oil, soybean oil, and coco-caprylate/caprate, the blend present in the composition in a total amount from about 40% to about 50%, by weight, based on the total weight of the composition.

16. The hydrating cosmetic composition according to claim 1, wherein glyceryl stearate is present in the composition in an amount from about 2% to about 20%, by weight, based on the total weight of the composition.

17. The hydrating cosmetic composition according to claim 1, wherein the optional ingredients are selected from the group consisting of citric acid, tocopherol, and fragrance, wherein the composition is essentially free of one or more of paraffin waxes, ozokerite, petroleum derived compounds, synthetic surfactants that include polglyceryl esters of fatty acids, mineral oil and lanolin.

18. The hydrating cosmetic composition according to claim 1, wherein the composition is essentially free of hydrogenated polyisobutene and PEG-30 dipolyhydroxystearate.

19. A hydrating cosmetic composition for keratinous substrates, consisting of:
a stabilized anhydrous balm consisting of:
  a) at least one glycol humectant that includes glycerin, wherein the glycerin is present in an amount from at least about 10%, by weight, based on the total weight of the composition, the glycol humectant dispersed in a stabilized anhydrous fatty phase; and
  b) a stabilized anhydrous fatty phase consisting of:
    i) at least one plant derived butter, wherein the at least one plant derived butter includes one or more of shea butter having a melting point that is in the range from about 45° C. to about 51° C. and present in an amount from about 1% to about 30%, by weight, based on the total weight of the composition, shea butter having a melting point that is in the range from about 30° C. to about 35° C. and present in an amount from about 1% to about 30%, by weight, based on the total weight of the composition cacao butter present in an amount from about 1% to about 30%, by weight, based on the total weight of the composition, murumuru butter present in an amount from about 1% to about 30%, by weight, based on the total weight of the composition, cupuacu butter present in an amount from about 1% to about 30%, by weight, based on the total weight of the composition, and mango butter present in an amount from about 1% to about 30%, by weight, based on the total weight of the composition, and wherein the at least one plant derived butter is present in a total amount from at least about 20%, by weight, based on the total weight of the composition;
    ii) a blend of structuring waxes that includes at least one nature derived wax and hydrogenated vegetable oil, the structuring waxes present in a ratio of nature derived wax to hydrogenated vegetable oil in a range from about 3:1 to about 1:3, wherein the at least one nature derived wax in the blend of structuring waxes includes rice bran wax, present in the composition in an amount that is from at least about 0.75%, by weight, based on the total weight of the composition, and wherein hydrogenated vegetable oil is present in the composition in an amount that is from about 0.75% to not more than about 3%, by weight, based on the total weight of the composition;

iii) a blend of fatty compounds that includes glyceryl dibehenate, tribehenin and glyceryl behenate, with or without a solvent, and two or more fatty compounds selected from triglycerides and plant derived oils having a chain length from and including C8 to C24, the blend of fatty compounds, in combination, present in the composition in an amount from about 10% to about 50%, by weight, based on the total weight of the composition; and iv) a surfactant that includes glyceryl stearate; and c) optionally, one or more ingredients selected from the group consisting of chelating agents, anti-microbial components, antioxidants, vitamins, vitamin derivatives fragrances, and combinations thereof;

wherein the stabilized anhydrous balm is characterized as being stabilized as demonstrated by an absence of one or more of visible droplets and visible crystals after about eight weeks at 45° C.

20. A hydrating cosmetic composition for keratinous substrates, consisting of:
a stabilized anhydrous balm consisting of:
a) at least one glycol humectant that includes glycerin, wherein the glycerin is present in an amount from at least about 10%, by weight, based on the total weight of the composition, the glycol humectant dispersed in a stabilized anhydrous fatty phase; and
b) a stabilized anhydrous fatty phase consisting of:
i) at least one plant derived butter, wherein the at least one plant derived butter includes one or more of shea butter having a melting point that is in the range from about 45° C. to about 51° C. and present in an amount from about 1% to about 30%, by weight, based on the total weight of the composition, shea butter having a melting point that is in the range from about 30° C. to about 35° C. and present in an amount from about 1% to about 30%, by weight, based on the total weight of the composition cacao butter present in an amount from about 1% to about 30%, by weight, based on the total weight of the composition, murumuru butter present in an amount from about 1% to about 30%, by weight, based on the total weight of the composition, cupuacu butter present in an amount from about 1% to about 30%, by weight, based on the total weight of the composition, and mango butter present in an amount from about 1% to about 30%, by weight, based on the total weight of the composition, and wherein the at least one plant derived butter is present in a total amount from at least about 20% to about 30%, by weight, based on the total weight of the composition;

ii) a blend of structuring waxes that includes at least one nature derived wax and hydrogenated vegetable oil, the structuring waxes are present in a ratio of hydrogenated vegetable oil to nature derived wax in a range from about 3:1 to about 1:3, wherein the at least one nature derived wax in the blend of structuring waxes includes rice bran wax present in the composition in an amount that is from about 0.75% to about 10%, by weight, based on the total weight of the composition, and wherein hydrogenated vegetable oil is present in the composition in an amount that is from about 0.75% to about 10%, by weight, based on the total weight of the composition;

iii) a blend of fatty compounds that includes glyceryl dibehenate, tribehenin and glyceryl behenate, with or without a solvent, and two or more fatty compounds selected from triglycerides and fatty plant derived oils having a chain length from and including C8 to C24, wherein the glyceryl dibehenate, tribehenin and glyceryl behenate, in combination, is present in an amount from about 6% to about 10%, by weight, based on the total weight of the composition, and wherein each of glyceryl dibehenate, tribehenin and glyceryl behenate, individually, is present in an amount from about 0.5% to about 3%, by weight, based on the total weight of the composition, and wherein the blend of fatty compounds includes caprylic-capric triglycerides, C10-C18 triglycerides, sunflower seed oil, soybean oil, and coco-caprylate/caprate, the blend of fatty compounds present in the composition in a total amount from about 40% to about 50%, by weight, based on the total weight of the composition; and iv) a surfactant that includes glyceryl stearate present in the composition in an amount from about 6% to about 10%, by weight, based on the total weight of the composition; and c) optionally, one or more ingredients selected from the group consisting of chelating agents, anti-microbial components, antioxidants, vitamins, vitamin derivatives fragrances, and combinations thereof wherein the stabilized anhydrous balm is characterized as being stabilized as demonstrated by an absence of one or more of visible droplets and visible crystals after about eight weeks at 45° C., and wherein the composition is essentially free of one or more of paraffin waxes, ozokerite, petroleum derived compounds synthetic surfactants that include polglyceryl esters of fatty acids, mineral oil and lanolin.

\* \* \* \* \*